United States Patent
Marsh et al.

(10) Patent No.: US 10,117,819 B2
(45) Date of Patent: *Nov. 6, 2018

(54) COMPOSITION FOR HAIR FRIZZ REDUCTION

(71) Applicant: The Procter & Gamble Company, Cincinnati, OH (US)

(72) Inventors: Jennifer Mary Marsh, Deerfield Township, OH (US); Supriya Punyani, Singapore (SG); MuiSlang Soh, Singapore (SG); Jiazhen Zhang, Singapore (SG); Brian Xiaoqing Song, Mason, OH (US); Tiffany Tien-Yun Yang, Loveland, OH (US)

(73) Assignee: The Procter and Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/959,234

(22) Filed: Dec. 4, 2015

(65) Prior Publication Data

US 2016/0158128 A1   Jun. 9, 2016

Related U.S. Application Data

(60) Provisional application No. 62/088,029, filed on Dec. 5, 2014.

(51) Int. Cl.
*A61K 8/44*   (2006.01)
*A61K 8/362*   (2006.01)
(Continued)

(52) U.S. Cl.
CPC ............ *A61K 8/41* (2013.01); *A61K 8/25* (2013.01); *A61K 8/34* (2013.01); *A61K 8/36* (2013.01);
(Continued)

(58) Field of Classification Search
CPC ........ A61K 8/362; A61K 8/365; A61K 8/368; A61K 8/445
See application file for complete search history.

(56) References Cited

U.S. PATENT DOCUMENTS 2,392,314 A   1/1946   Dalton
4,496,536 A   1/1985   Moller et al.
(Continued)

FOREIGN PATENT DOCUMENTS

DE   19536423 A1   4/1996
DE   102011089357 A1   8/2012
(Continued)

OTHER PUBLICATIONS

Special Chem ([retrieved from on-line website http://cosmetics.specialchem.com/inci/hydroxyethyl-urea, pp. 1-2, last visit Sep. 10, 2016].*
(Continued)

*Primary Examiner* — Ernst V Arnold
*Assistant Examiner* — Kyung S Chang
(74) *Attorney, Agent, or Firm* — Linda M. Sivik

(57) ABSTRACT

The present invention is directed to a rinse-off conditioner composition for hair frizz reduction comprising from about 0.2% to about 20% of a moisture control material or mixture of moisture control materials wherein the moisture control material is selected from one or more of the following:

(Continued)

wherein R' is —COOY, sulfonic acid, or C=CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH=CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0; and at least about a 4% fizz reduction vs. a control composition without the moisture control material.

16 Claims, 1 Drawing Sheet

(51) Int. Cl.
| | | |
|---|---|---|
| A61K 8/365 | (2006.01) | |
| A61K 8/368 | (2006.01) | |
| A61K 8/41 | (2006.01) | |
| A61K 8/25 | (2006.01) | |
| A61K 8/34 | (2006.01) | |
| A61K 8/36 | (2006.01) | |
| A61Q 5/12 | (2006.01) | |

(52) U.S. Cl.
CPC .............. *A61K 8/362* (2013.01); *A61K 8/365* (2013.01); *A61K 8/368* (2013.01); *A61K 8/445* (2013.01); *A61Q 5/12* (2013.01); *A61K 2800/70* (2013.01)

(56) References Cited

U.S. PATENT DOCUMENTS

| | | |
|---|---|---|
| 4,678,475 A | 7/1987 | Hoshowski et al. |
| 5,102,655 A | 4/1992 | Yoshihara et al. |
| 5,384,114 A | 1/1995 | Dowell et al. |
| 5,587,155 A | 12/1996 | Ochiai et al. |
| 5,688,495 A | 11/1997 | Rosen et al. |
| 6,001,340 A | 12/1999 | Rosen et al. |
| 6,156,299 A | 12/2000 | Rosen et al. |
| 6,294,186 B1 | 9/2001 | Beerse et al. |
| 6,495,498 B2 | 12/2002 | Niemiec et al. |
| 6,858,202 B2 | 2/2005 | Niemiec et al. |
| 6,908,889 B2 | 6/2005 | Niemiec et al. |
| 7,527,654 B2 | 5/2009 | Plos |
| 8,512,686 B2 | 8/2013 | Morioka |
| 8,968,712 B2 | 3/2015 | Tanaka |
| 9,216,146 B2 | 12/2015 | Tanaka |
| 9,259,070 B2 | 2/2016 | Fischer et al. |
| 9,265,321 B2 | 2/2016 | Fischer et al. |
| 9,271,908 B2 | 3/2016 | Allef et al. |
| 9,905,528 B2 | 2/2018 | Kira et al. |
| 2003/0022936 A1 | 1/2003 | Milbradt et al. |
| 2003/0143173 A1 | 7/2003 | Buck |
| 2003/0215405 A1 | 11/2003 | Parker et al. |
| 2003/0223952 A1 | 12/2003 | Wells et al. |
| 2004/0120911 A1 | 6/2004 | Shah et al. |
| 2004/0180016 A1 | 9/2004 | Buck |
| 2004/0261198 A1 | 12/2004 | Kainz et al. |
| 2005/0136015 A1 | 6/2005 | McKie et al. |
| 2005/0143268 A1 | 6/2005 | Midha et al. |
| 2005/0169869 A1 | 8/2005 | Laurent et al. |
| 2005/0175567 A1* | 8/2005 | Khoshdel ............... A61K 8/347 424/70.2 |
| 2005/0196369 A1 | 9/2005 | Ueyama et al. |
| 2005/0266034 A1 | 12/2005 | Muller et al. |
| 2006/0165636 A1 | 7/2006 | Hasebe et al. |
| 2006/0204466 A1 | 9/2006 | Littau et al. |
| 2006/0286059 A1 | 12/2006 | Yang et al. |
| 2007/0104667 A1 | 5/2007 | Mondet et al. |
| 2007/0149423 A1 | 6/2007 | Warr et al. |
| 2007/0261179 A1 | 11/2007 | Dorkel et al. |
| 2008/0138438 A1 | 6/2008 | Taylor et al. |
| 2008/0194454 A1 | 8/2008 | Morgan et al. |
| 2009/0169502 A1 | 7/2009 | Quadir |
| 2009/0324531 A1 | 12/2009 | Okada et al. |
| 2010/0297051 A1 | 11/2010 | Feuillette |
| 2010/0300472 A1 | 12/2010 | Malle et al. |
| 2010/0330007 A1 | 12/2010 | Spindler et al. |
| 2011/0003016 A1 | 1/2011 | Burry et al. |
| 2011/0269658 A1 | 11/2011 | Dihora et al. |
| 2012/0070398 A1 | 3/2012 | Nagano et al. |
| 2012/0093751 A1 | 4/2012 | Nagano et al. |
| 2012/0308506 A1 | 12/2012 | Oku et al. |
| 2013/0064908 A1 | 3/2013 | Noh |
| 2013/0125915 A1 | 5/2013 | Nagase et al. |
| 2013/0164390 A1 | 6/2013 | Richards et al. |
| 2013/0259817 A1 | 10/2013 | Uehara et al. |
| 2013/0259819 A1 | 10/2013 | Uehara et al. |
| 2013/0306095 A1 | 11/2013 | Syed |
| 2014/0079660 A1 | 3/2014 | Doi |
| 2014/0154197 A1 | 6/2014 | Swaile et al. |
| 2014/0179645 A1 | 6/2014 | Arndt |
| 2015/0174052 A1 | 6/2015 | Mette et al. |
| 2015/0313832 A1 | 11/2015 | Hilvert et al. |
| 2015/0359716 A1 | 12/2015 | Marsh et al. |
| 2015/0374609 A1 | 12/2015 | Cetti et al. |
| 2016/0015608 A1 | 1/2016 | Marsh et al. |
| 2016/0022558 A1 | 1/2016 | Kunin et al. |
| 2016/0158128 A1 | 6/2016 | Marsh et al. |
| 2016/0158135 A1 | 6/2016 | Marsh et al. |
| 2016/0175209 A1 | 6/2016 | Walker et al. |
| 2016/0228342 A1 | 8/2016 | Rose |
| 2016/0287494 A1 | 10/2016 | Punyani et al. |
| 2016/0287495 A1 | 10/2016 | Punyani et al. |
| 2017/0216172 A1 | 8/2017 | Carballada et al. |
| 2017/0290755 A1 | 10/2017 | Soh et al. |

FOREIGN PATENT DOCUMENTS

| | | | |
|---|---|---|---|
| DE | 102011089357 A1 | 8/2012 | |
| EP | 1787680 A2 | 5/2007 | |
| EP | 1326577 B1 | 10/2008 | |
| EP | 2036536 A1 | 3/2009 | |
| EP | 2392314 A1 | 12/2011 | |
| FR | 2931659 B1 | 3/2011 | |
| FR | 2968946 B1 | 4/2013 | |
| GB | 816750 | 7/1959 | |
| JP | S63156711 A | 6/1988 | |
| JP | H06256137 A | 9/1994 | |
| JP | 309959 B2 | 2/2000 | |
| JP | 3026213 B2 | 3/2000 | |
| JP | 2001122737 A | 5/2001 | |
| JP | 2005145883 A | 6/2005 | |
| JP | 2005194261 A | 7/2005 | |
| JP | 3843051 B2 | 11/2006 | |
| JP | 2007-070469 A | 3/2007 | |
| JP | 4329097 B2 | 9/2009 | |
| JP | 4452523 B2 | 4/2010 | |
| JP | 4625357 B2 | 2/2011 | |
| JP | 4679893 B2 | 5/2011 | |
| JP | 4883261 B2 | 2/2012 | |
| JP | 5086539 B2 | 11/2012 | |
| JP | 5228338 B2 | 7/2013 | |
| JP | 2014097931 A | 5/2014 | |
| JP | 5779399 B2 | 9/2015 | |
| WO | 01/28338 A2 | 4/2001 | |
| WO | 01/28339 A2 | 4/2001 | |
| WO | WO 0128339 A2 * | 4/2001 | ............. A01N 43/36 |
| WO | WO2011074134 A1 | 6/2011 | |
| WO | WO2012131848 A1 | 10/2012 | |
| WO | 2014/002668 A1 | 1/2014 | |
| WO | WO2014100970 A1 | 7/2014 | |

OTHER PUBLICATIONS

John Frieda Frizzease conditioner product (John Frieda, Frizzease smooth start conditioner—https://www.johnfrieda.com/en-UK/

(56) References Cited

OTHER PUBLICATIONS products/frizz-ease/smooth-start-conditioner.html, last visit date: Jan. 17, 2018) (Year: 2018).*
"Infusion 23 (Colour) Ologie Leave-In Treatment", Procter & Gamble, Feb. 1, 2007, Mintel.
"De-Frizz Leave-In Treatment", Quality Collor Cosmeticos, May 1, 2014, Mintel.
PCT Invitation to Pay Additional Fees and, Where Applicable, Protest Fee for PCT/US2015/036195, dated Oct. 7, 2015.
Invitation to Pay Additional Fees and, Where Applicable, Protest Fee for PCT/US2015/036192 dated Jan. 4, 2016.
Invitation to Pay Additional Fees and, Where Applicable, Protest Fee for PCT/US2015/063893, dated Feb. 8, 2016.
PCT Invitation to Pay Additional Fees and, Where Applicable, Protest Fee for PCT/US2015/063888 dated Mar. 9, 2016.
All Final and Non-Final Office Actions for U.S. Appl. No. 14/677,578, P&G Case 13769.
All Final and Non-Final Office Actions for U.S. Appl. No. 14/677,636, P&G Case 13770.
All Final and Non-Final Office Actions for U.S. Appl. No. 14/742,136, P&G Case 13355M.
All Final and Non-Final Office Actions for U.S. Appl. No. 14/742,145, P&G Case 13356M.
All Final and Non-Final Office Actions for U.S. Appl. No. 14/755,567, P&G Case 13461M.
All Final and Non-Final Office Actions for U.S. Appl. No. 14/959,243, P&G Case 13641M.
All Final and Non-Final Office Actions for U.S. Appl. No. 15/093,075, P&G Case AA1008.
All Final and Non-Final Office Actions for U.S. Appl. No. 15/367,356, P&G Case 14116.
All Final and Non-Final Office Actions for U.S. Appl. No. 15/367,363, P&G Case 14117.
All Final and Non-Final Office Actions for U.S. Appl. No. 15/367,369, P&G Case 14118.
Anonymous: "Spotlight on Apricot Oil, Black Girl with Long Hair", Apr. 5, 2013, Retrieved from the internet: URL: http://blackgirllonghair.com/2013/04/spotlight -on-apricot-oil/, Retrieved Jun. 2, 2016.
Khan, H., "5 ways to straighten your hair without heat", Hair Beauty Tips, Jul. 12, 2013, pp. 1-4.
Medline Plus "Aging changes in hair and nails", US National Library of Medicine, Oct. 27, 2014, pp. 1-3.
PCT International Search Report and Written Opinion for PCT/US2015/036192 dated Mar. 21, 2016.
PCT International Search Report and Written Opinion for PCT/US2015/036195 dated Dec. 16, 2015.
PCT International Search Report and Written Opinion for PCT/US2016/025827 dated Jun. 24, 2016.
PCT International Search Report and Written Opinion for PCT/US2016/064604 dated Apr. 10, 2017.
PCT International Search Report and Written Opinion for PCT/US2016/064606 dated Apr. 12, 2017.
PCT International Search Report and Written Opinion for PCT/US2016/064608 dated Apr. 18, 2017.
PCT Invitation to Pay Additional Fees and, Where Applicable, Protest Fee for PCT/US2015/064608 dated Feb. 20, 2017, 9 pages.
PCT Invitation to Pay Additional Fees and, Where Applicable, Protest Fee for PCT/US2016/064604 dated Feb. 15, 2017, 10 pages.
PCT Invitation to Pay Additional Fees and, Where Applicable, Protest Fee for PCT/US2016/064606 dated Feb. 20, 2017, 14 pages.
Retrieved from internet: http://cosmetics.specialchem.com/inci/hydroxyethyl-urea, last visit May 10, 2017.
All Final and Non-Final Office Actions for U.S. Appl. No. 15/949,539, P&G Case 14768.
All Final and Non-Final Office Actions for U.S. Appl. No. 15/949,555, P&G Case 14769.

* cited by examiner

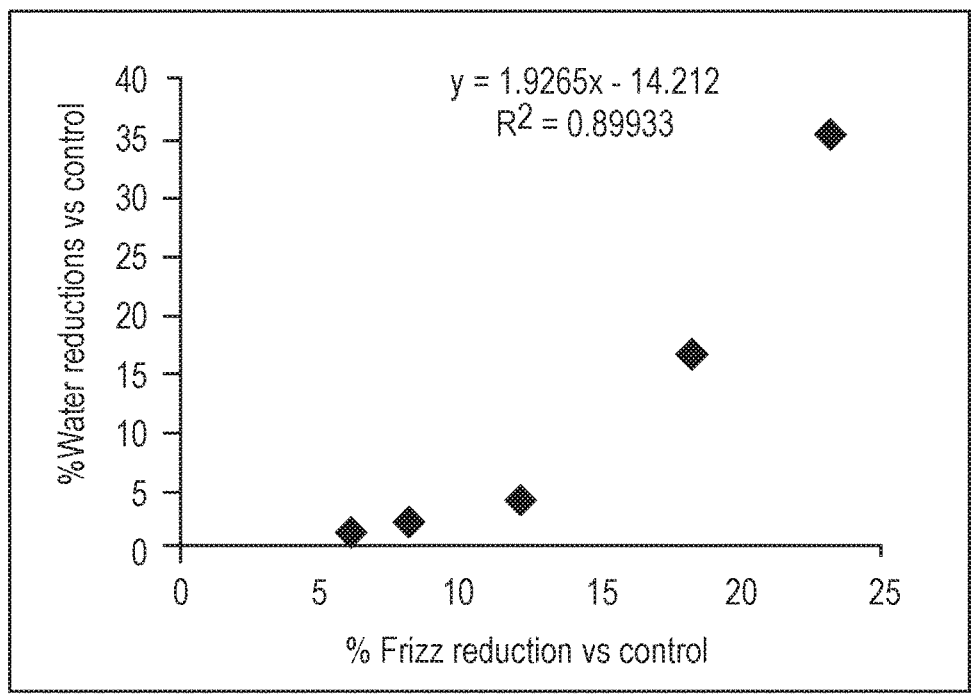

COMPOSITION FOR HAIR FRIZZ REDUCTION

FIELD OF THE INVENTION

The present invention relates to a rinse off conditioner composition comprising one or more materials useful for treating hair frizz.

BACKGROUND OF THE INVENTION

Hair frizz is described by consumers as the appearance of unruly fibers at the top of the scalp and tips of hair as well as an increased volume through the bulk of the hair. Generally they see this frizz on days when there is humid weather and the level of moisture in the air is high. The appearance of frizz is undesired and it is often associated with a loss of shine and smoothness. The appearance of frizz and loss of shine and smoothness are associated with a perception of poor hair health. The basic mechanism causing frizz in high humid environments is that at high humidity water penetrates into hair and changes the chemical bond interactions inside the hair. During styling, the consumer will create a 'wet set' where hair is blow dried or flat ironed to create the desired shape. During drying, water is evaporated from hair and hydrogen bonds are formed between the protein peptide chains holding the style in place. As moisture diffuses into hair the hydrogen bonds are broken and hair returns back to its natural shape. For consumers who straighten their hair by blow drying or flat ironing this return to a curled style is associated with a loss of alignment and increased volume. In addition, at high moisture levels in hair the fiber diameter increases which also increases the overall volume of hair.

The typical strategy to prevent frizz is to formulate conditioner products with surface-depositing materials such as silicone, oils, conditioning silicone etc. which make hair more hydrophobic and decrease inter-fiber interactions. At high levels these materials can also provide increased cohesive forces holding fibers together to prevent frizz from occurring. With these materials depositing on the hair surface a greasy look and feel is typically experienced, which is an undesired trade-off of frizz reduction.

Consequently, a need exists for a conditioner product that combines effective frizz control with additional hair benefits that the consumer can notice and feel and, at the same time, is delightful to use without having a sticky or greasy feel.

SUMMARY OF THE INVENTION

In an embodiment, a rinse-off conditioner composition for hair frizz reduction comprising: from about 0.2% to about 20% of a moisture control material or mixture of moisture control materials wherein the moisture control material is selected from one or more of the following:

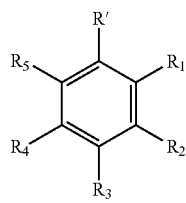

wherein R' is —COOY, sulfonic acid, or C=CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH=CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0; and at least about a 4% fizz reduction vs. a control composition without the moisture control material.

Without being bound by theory, the materials in the conditioner treatment composition of the present invention provide excellent frizz performance without a negatively affecting hair feel. These materials prevent water uptake into hair under high humidity conditions, reducing the negative impact of frizz. By providing frizz benefits by penetrating the hair fiber as opposed to depositing on the hair surface, the frizz benefit is not associated by negative hair feel, which is typically observed with current commercial anti-frizz products. These and additional features provided by the embodiments of the present invention will be more fully understood in view of the following detailed description.

BRIEF DESCRIPTION OF THE DRAWINGS

FIG. 1 is graph depicting that there is a monotonic correlation between % water reduction and % frizz reduction.

DETAILED DESCRIPTION OF EMBODIMENTS OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity (RH), unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application" as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit "Control composition" is a composition that is used for comparison to the inventive composition in terms of performance. Typically, the control composition and the inventive composition are very similar in terms of ingredients and concentrations with the difference being that control composition does not include the material or materials that constitute the invention. Thus, the inventive material(s) that are present in the inventive composition are either substituted by the carrier in the control composition or by a material that is common in the art at the time of the invention.

"Rinse-off" in reference to compositions, means compositions intended to be applied to keratinous substrate and subsequently removed by washing, rinsing or wiping within a few minutes or less from the application. These "rinse-off" compositions are to be distinguished from "leave-on" compositions, which are intended to be applied to and allowed to remain on the keratinous tissue.

The most common hair care rinse-off compositions are shampoos and rinse-off conditioners. Shampoos contain detersive surfactants and they are used for cleansing hair, while rinse-off conditioners are typically used after shampoo, they are substantially free of detersive surfactants, they contain conditioning agents to improve hair feel, reverse hair damage and protect against further damage.

"Leave-on," in reference to compositions, means compositions intended to be applied to and allowed to remain on the keratinous tissue. These leave-on compositions are to be distinguished from compositions, which are applied to the hair and subsequently (in a few minutes or less) removed either by washing, rinsing, wiping, or the like. Leave-on compositions exclude rinse-off applications such as shampoos, rinse-off conditioners, facial cleansers, hand cleansers, body wash, or body cleansers. The leave-on compositions may be substantially free of cleansing or detersive surfactants. For example, "leave-on compositions" may be left on the keratinous tissue for at least 15 minutes. For example, leave-on compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

"Soluble" means at least about 0.1 g of solute dissolves in 100 ml of solvent, at 25° C. and 1 atm of pressure.

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. The weight average molecular weight may be measured by gel permeation chromatography. "QS" means sufficient quantity for 100%.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. Polymers made from two or more different types of monomers are called copolymers. The distribution of the different monomers can be calculated statistically or block-wise—both possibilities are suitable for the present invention. Except if stated otherwise, the term "polymer" used herein includes any type of polymer including homopolymers and copolymers.

The mechanism of action for frizz generation involves moisture from the environment being absorbed by hair and occupying hydrogen bonding sites within hair, including those on the peptide backbone and also associated with acidic and basic side chains of amino acid residues such as lysine, arginine and glutamic acid. This internal water replaces hydrogen bonds that had been created during styling that hold hair in a desired configuration. As a consequence, hair returns to its natural shape which typically leads to unwanted wave, loss of alignment and frizz. In addition, uptake of water by these hydrogen bonding sites swells the hair fiber causing style expansion, which is another indicator of fizz. Without being bound by theory, the materials covered by this invention will replace water at the hydrogen bond sites inside hair and prevent water uptake. Reduction of water inside hair will lead to a reduction in the appearance of frizz under high humidity conditions. Because the mechanism of action is related to the space inside the hair fibers, there are no feel negatives, such as, for example, greasy or oily feel associated with the benefit. The reduction in water uptake is measured using Dynamic Vapor Sorption (DVS) method, which measures a weight increase of hair equilibrated at 0% Relative Humidity (RH) versus 90% RH. Significant frizz benefit is measured on hair treated by materials that caused a reduction in water uptake of higher than 5% versus control hair that is not treated with such materials. The treatment involved the application of a 2% w/w solution of the material in 50:50 water:ethanol solvent.

Preferred materials include salicylic acid, 2,3-dihydroxybenzoic acid, 2,6-dihydroxybenzoic acid, 3-aminobenzoic acid, gallic acid, ethyl gallate, 5-chlorosalicylic acid, trans-ferulic acid, p-coumaric acid, ricinoleic acid, isovaleric acid, isobutyric acid, 2-hexyl-1-decanol, phytol and sorbitan caprylate. These materials are chosen from Molecular Class I and/or Molecular Class II or can also be used in combination to increase the size of the benefit.

In an embodiment of the present invention, the concentration of the Moisture Control Material or the concentration of the mixture of Moisture Control Material in a hair conditioner composition is from about 0.2% to about 20%, in an embodiment from about 0.5% to about 8.0%, and in a further embodiment from about 0.5% to about 5.0%.

Molecular Class I: Polar, Acidic Compounds with the Following Properties:

Protein Binding (PB)>20 AND Molecular Volume (Mol. Vol).<500 AND log P<3 AND Hydrogen-binding (H-binding)>10 AND pKa<5.0, wherein PB is % protein binding, Mol. Vol is molecular volume (in Å$^3$); log P is n-octanol/water partition coefficients. These properties can be calculated using Volsurf software (http://www.moldiscovery.com/soft_volsurf.php). H-bond is the energy from hydrogen bonds between molecules from Hansen Solubility Parameters and pKa value is a logarithmic measure of the acid dissociation constant.

| Name (1% wt/vol) | PB | Mol. Vol. | log P | pKa | H-bond (MPa^½) | % Water Reduction |
|---|---|---|---|---|---|---|
| 2,4-Dihydroxybenzoic acid | 28 | 324 | 1.5 | 3.2 | 23 | 30 |
| 3-Hydroxybenzoic Acid | 38 | 314 | 1.6 | 4.3 | 20 | 20 |
| Gallic acid | 23 | 337 | 0.9 | 4.4 | 23 | 15 |
| 3-Aminobenzoic acid | 41 | 326 | 0.9 | 3.6 | 16 | 12 |
| 4-Aminobenzoic acid | 42 | 323 | 0.9 | 3.5 | 16 | 12 |
| 2,5-Dihydroxybenzoic acid | 31 | 329 | 1.6 | 2.9 | 23 | 27 |
| 3,4-Dihydroxybenzoic acid | 27 | 327 | 0.9 | 4.4 | 23 | 20 |
| 3,5-Dihydroxybenzoic acid | 27 | 327 | 0.9 | 4.1 | 23 | 15 |
| 2,6-Dihydroxybenzoic acid | 37 | 326 | 1.6 | 2.1 | 23 | 35 |
| 5-Chlorosalicylic acid | 56 | 361 | 2.3 | 3.0 | 21 | 28 |
| Salicylic acid | 44 | 320 | 2.1 | 3.1 | 20 | 18 |
| Trans-Ferulic Acid | 50 | 451 | 1.5 | 4.5 | 19 | 6 |
| p-Coumaric acid | 46 | 391 | 1.6 | 4.5 | 20 | 8.8 |
| 4-Hydroxybenzene-sulphonic acid | 55 | 271 | 1.5 | 2.7 | 22 | 26 |
| 3-Chloro-4-hydroxybenzoic acid | 49 | 356 | 2.1 | 4.1 | 20 | 11 |
| 3,5-Dichloro-4-hydroxybenzoic acid | 51 | 397 | 2.8 | 3.8 | 20 | 15 |
| 2,5 Dihydroxyterephthalic acid | 20 | 375 | 1.1 | 2.1 | 22 | 18 |
| 3-Aminophenol | 45 | 284 | 0.6 | 4 | 17 | 14 |
| 3-Hydroxyanilinium chloride | 32 | 280 | 0.6 | 4 | 17 | 16 |
| 2-Aminophenol | 49 | 288 | 1.0 | 4 | 17 | 14 |
| 4-Aminophenol | 39 | 284 | 0.6 | 4 | 17 | 10 |
| N-4-Hydroxyphenylglycine | 37 | 388 | 1.3 | 3 | 13 | 15 | b) Molecular Class II:

Weakly polar to non-polar, weakly to non-acidic compounds that have the following properties: PB>10 AND Mol. Vol.<1500 AND log P>0.5 AND pKa≥5 AND H-binding>4, wherein PB is % protein binding, Mol. Vol is molecular volume (in Å$^3$); log P is n-octanol/water partition coefficients. These properties can be calculated using Volsurf software (http://www.moldiscovery.com/soft_volsurf.php). H-bond is the energy from hydrogen bonds between molecules from Hansen Solubility Parameters and pKa value is a logarithmic measure of the acid dissociation constant.

| Name | PB | Mol. Vol. | logP | pKa | H-bond (MPa^½) | % water reduction |
|---|---|---|---|---|---|---|
| 2-Hydroxyethyl salicylate | 45 | 419 | 1.5 | 8.3 | 19.1 | 10 |
| Ethyl gallate | 43 | 431 | 1.4 | 8.7 | 22.6 | 17 |
| Oleic Acid | 100 | 832 | 7 | 5 | 6.4 | 14 |
| Ricinoleic acid | 84 | 841 | 5.9 | 5 | 17.8 | 8.8 |
| Isovaleric acid | 29 | 295 | 1.3 | 5 | 9.7 | 15 |
| Isobutyric acid | 15 | 254 | 1 | 5 | 10.4 | 5 |
| 2-Hexyl-1-decanol | 87 | 745 | 6.8 | 15 | 10.1 | 11 |
| Phytol | 100 | 874 | 8.0 | 13 | 9.6 | 14 |
| Sorbitan caprylate | 32 | 695 | 1.3 | 12 | 21.8 | 11 |
| Glyceryl monooleate | 96 | 974 | 6.27 | 12.8 | 16.2 | 5 |
| Isostearyl isostearate | 100 | 1527 | 14.7 | 14 | 4.2 | 11 |
| Ethyl linoleate | 82 | 903 | 7.71 | 7.8 | 5.1 | 8 |
| Isopropyl myristate | 97 | 798 | 6.99 | 8.8 | 5.0 | 12 |
| Octyl salicylate | 82 | 646 | 5.4 | 7.1 | 11.7 | 14 |

A Class I having the structure selected from:
1) Class I having the structure selected from:

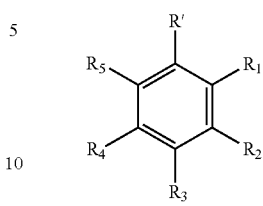

wherein R' is —COOY, sulfonic acid, or —C=CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH=CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0;
2) Class II having the structure selected from:

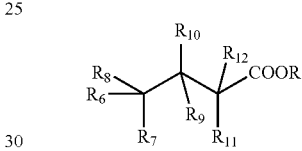

wherein R is hydrogen or metal ion, $R_6$ is methyl, ethyl, propyl, alkenyl or phenyl having less than 12 carbon atoms and wherein $R_7$, $R_8$, $R_9$, $R_{10}$, $R_{11}$, $R_{12}$ are hydrogen, methyl, ethyl, propyl, phenyl, hydroxyl, methoxy or ethoxy groups;
b)

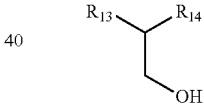

an alcohol wherein R13 is an alkyl, alkenyl, straight or branched carbon chains and; and wherein R14 is hydrogen, hydroxyl, alkyl, methyl, ethyl and propyl wherein the structure of such alcohol contains less than 20 total carbon atoms;
  c) An alcohol comprising an unsaturated double bond in the C2 position. A non limiting example would be phytol.
  d) an alkyl-substituted glycol wherein the structure of such alkyl substituted glycol contains less than 20 carbon atoms;
  e) a monoalkyl or dialkyl substituted glycerin or mono- or di-esters of glycerin with fatty acids wherein the structure of such monoalkyl- or dialkyl-substituted glycerin or glycerin esters contains less than 20 total carbon atoms;
  f)

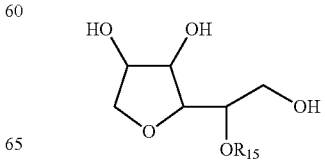

wherein $R_{15}$ could be hydrogen, alkyl, alkenyl, phenyl group and wherein the structure of the $R_{13}$ group contains less than 20 carbon atoms;
- g) a fatty acid ester containing from 15-40 total carbon atoms and wherein the moisture control material of Class II is weakly to non-acidic and further wherein the moisture control material of Class II has protein binding higher than 10 and molecular volume lower than 1500 and log P higher than 0.5 and pKa of 5 or higher and hydrogen-binding higher than 4.

pH of Compositions

Below is the data of the difference of % water reduction of hair treated with leave on composition containing 1% salicylic acid in ethanol:water (50:50) at various values of pH vs control (hair treated with composition of ethanol:water (50:50). As shown in below table, at lower pH, the present invention demonstrates improved performance compared to higher pH.

|  | Formula Example | | | |
| --- | --- | --- | --- | --- |
| Raw Material | pH 3 | pH 4.2 | pH 7 | pH 10 |
| Distilled Water | QS | QS | QS | QS |
| Ethanol | 50.0 | 50.0 | 50.0 | 50.0 |
| Salicylic acid | 1.0 | 1.0 | 1.0 | 1.0 |
| Final pH | 3.2 | 4.2 | 7 | 10 |
| % Water Reduction | 30 | 27 | 22 | 15 |

In an embodiment of the present invention, the pH of a composition of the present invention comprising material from Molecular Class I may be in the range of from about 1 to about 9, in another embodiment a pH of from about 2 to about 7, in a further embodiment a pH of from about 4 to about 5.5.

In an embodiment of the present invention, the Moisture control Material is a carboxylic acid ester. In an embodiment, the carboxylic acid ester is based on a fatty acid wherein the molecule of the fatty acid comprises of more than 14 carbon atoms. Non-limiting examples of such esters are isostearyl isostearate, methyl stearate, methyl palmitate, and methyl oleate. In another embodiment of the present invention, the carboxylic acid ester is part of a mixture of materials prepared via the reaction of natural oils using methanol. Non-limiting examples of such mixture is the mixture that is produced by the product of the reaction of refined palm kernel oil with methanol, followed by fractionation via distillation. A commercial product that meets this description is the Heavy Cut Ester CE-1875 (supplied by P&G Chemicals with CAS Number 6772-38-3) containing ingredients such as methyl stearate, methyl palmitate, methyl oleate as major ingredients, as well as methyl laurate, methyl myristate, methyl behenate and other materials as minor ingredients.

FORMULATIONS AND EXAMPLES

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

EXAMPLES

Rinse-Off Conditioner Composition Preparation:

The rinse-off conditioner compositions can be prepared by any conventional method well known in the art. The cationic surfactants and the fatty alcohols are mixed together and heated to from about 66° C. to about 85° C. to form an oil phase. Separately, the disodium EDTA, the Methylchloroisothiazolinone (preservative) and the water are mixed and heated to from about 20° C. to about 48° C. to form an aqueous phase. The oil phase is mixed into the water phase under high shear to form the gel matrix. The remaining of the components are added into the gel matrix with agitation. Then, the composition is cooled down to room temperature.

TABLE 1

Rinse-off Conditioner Formulations

| | | Formula Example | | | | | | | | |
| --- | --- | --- | --- | --- | --- | --- | --- | --- | --- | --- |
| Raw Material | Active % | Control (wt./wt.) % | I (wt./wt.) % | II (wt./wt.) % | III (wt./wt.) % | IV (wt./wt.) % | V (wt./wt.) % | VI (wt./wt.) % | VII (wt./wt.) % | VIII (wt./wt.) % |
| Benzenemethanaminium, N,N,N-trimethyl-, chloride (BTMAQ/Isopropyl Alcohol (IPA)[1] | 80 | 2.848 | 2.848 | 2.848 | 2.848 | 2.848 | 2.848 | 2.848 | 2.848 | 2.848 |
| Cetyl Alcohol[2] | 90 | 1.857 | 1.857 | 1.857 | 1.857 | 1.857 | 1.857 | 1.857 | 1.857 | 1.857 |
| Stearyl Alcohol[3] | 97 | 4.643 | 4.643 | 4.643 | 4.643 | 4.643 | 4.643 | 4.643 | 4.643 | 4.643 |
| Benzyl Alcohol[4] | 99 | 0.400 | 0.400 | 0.400 | 0.400 | 0.400 | 0.400 | 0.400 | 0.400 | 0.400 |
| Disodium EDTA, Dihydrate[5] | 99 | 0.127 | 0.127 | 0.127 | 0.127 | 0.127 | 0.127 | 0.127 | 0.127 | 0.127 |
| Methylchloroisothiazolinone (Kathon CG)[6] | 1.5 | 0.033 | 0.033 | 0.033 | 0.033 | 0.033 | 0.033 | 0.033 | 0.033 | 0.033 |
| Terminal Amino Silicone[7] | 90-100 | 0.3 | 0.3 | 0.3 | 0.3 | 0.3 | 0.3 | 0.3 | 0.3 | 0.3 |
| Perfume | | 0.550 | 0.550 | 0.550 | 0.550 | 0.550 | 0.550 | 0.550 | 0.550 | 0.550 |
| Salicylic acid[8] | 99.5 | 0 | 1.0 | 0.0 | 0.0 | 0.0 | 0.0 | 0 | 1 | 1 |
| 5-Chloro Salicylic acid[9] | 98 | 0 | 0 | 1.0 | 0 | 0 | 0 | 0 | 0 | 0 |
| 2,4 dihydroxybenzoic acid[10] | 97 | 0 | 0 | 0 | 1 | 0 | 0 | 0 | 0.15 | 0 |

TABLE 1-continued

Rinse-off Conditioner Formulations

| | | Formula Example | | | | | | | |
|---|---|---|---|---|---|---|---|---|---|
| Raw Material | Active % | Control (wt./wt.) % | I (wt./wt.) % | II (wt./wt.) % | III (wt./wt.) % | IV (wt./wt.) % | V (wt./wt.) % | VI (wt./wt.) % | VII (wt./wt.) % | VIII (wt./wt.) % |
| Isostearyl Isostearate[11] | 100 | 0 | 0 | 0 | 0 | 1 | 0 | 0 | 1 | 1 |
| 2-hexyldecanol[12] | 97 | 0 | 0 | 0 | 0 | 0 | 5 | 0 | 5 | 5 |
| Oleic acid[13] | 78 | 0 | 0 | 0 | 0 | 0 | 0 | 0.2 | 0 | 0.2 |
| Purified Water | | Q.S. | Q.S. | Q.S. | Q.S. | Q.S. | Q.S. | Q.S. | Q.S. | Q.S. |
| % Water Reduction versus Control at dose of 0.2 g of composition for 1 g of hair | | — | 0.6 | 0.8 | 0.2 | 0.8 | 0.9 | 0.1 | 2 | 3 |
| % Frizz Reduction | | | 7.69 | 7.79 | 7.48 | 7.79 | 7.84 | 7.43 | 8.41 | 8.93 |

[1]Supplied by Feixiang Chemicals (Zhangjingang) Co., Ltd.
[2]Supplied by P&G Chemicals
[3]Supplied by P&G Chemicals
[4]Supplied by Ineos Maastricht BV (Maastricht NL)
[5]Trilon BD Powder supplied by BASF SE (Ludwigshafen, DE)
[6]Kathon CG supplied by Rohm & Haas Co (Philadelphia US)
[7]Y-14945 supplied by Momentive Performance Materials
[8]Supplied by API Corpotration
[9]Supplied by Sigma Algrich
[10]Supplied by Sigma Algrich
[11]Crodamol ISIS supplied by Croda
[12]Isofol 16 supplied by Sasol (Brunsbuettel, DE)
[13]Greenolene 6928 supplied by Green Oleo Rinse-Off Conditioner Hair Treatment Protocol:

All testing are performed on Caucasian Damaged Frizzy hair switches weighing approximately 4.0 grams and having a length of approximately 6 inches. The hair switches are commercially available from IHIP (International Hair Importers). Three hair switches per rinse-off compositions per dosage are used. Each hair switch is washed with clarifying shampoo followed by a treatment with the rinse-off conditioner according to the following protocol.

An amount of 0.20 g of clarifying shampoo is spread via a syringe onto separate hair switch. That is, the dosage is 0.10 g of shampoo per g of hair. Each application consists of adding shampoo to the hair, milking for 30 seconds followed by rinsing for 30 seconds. Shampoo is then reapplied (0.1 g/g), milked for 30 seconds and rinsed for 30 seconds. Excess water is squeezed from the hair switches and then 0.1 g/g of the rinse-off conditioner is applied and milked for 30 seconds and then rinsed for 30 seconds.

This protocol is repeated for 5 times/cycles.

Evaluation Methods

The hair switches that are treated with the rinse-off conditioner compositions are evaluated using the following methodologies.

a. DVS Measurement

After the hair is exposed to the rinse-off conditioner treatment, it is blow-dried and analyzed for water absorption-desorption as a function of Relative Humidity (RH) according to the following procedure using Dynamic Vapor Sorption (DVS) method. More specifically, the hair switch is weighed and hold for equilibration at 0% RH for 16 hours. After the 16-hour period, the RH is increased to 10% and maintained at this level for 6 hours. Then, the RH is increased by 10% after every 6 hours interval until it reaches 90% RH. The % water reduction is calculated as follows:

A=Amount of water absorbed by the hair treated with composition containing the Moisture Control Material
B=Amount of water absorbed by the hair treated with control composition (only carrier) containing no Moisture Control Material $$\% \text{ Water reduction}=[(B-A)\times100]/B$$

The standard error for DVS measurement is less than 0.05 b. Determination of Frizz Reduction

The hair switches are thoroughly blow-dried after the treatment with rinse-off conditioner while holding the hair switch with all the hair fibers at the tip and then the hair switches are heat straightened by sectioning the hair into three parts and then heat with flat iron for 8 passes at 400-450 F. Hair switches are then kept at low humidity (between 20-25% RH) for equilibration for at least an hour. After the equilibration period, the hair switches are transferred to high humidity chamber (85-90% RH) for frizz assessment. Image of hair switches using a NIR Camera with parallel polarizers and are taken immediately after insertion of the hair into the high humidity chamber ($t_0$). Another image is taken after 3 hours ($t_{3h}$). The pixels are analyzed (selecting the entire hair switch) for 2D projection of volume (using vncviewer software). Then, the mean projected area is determined for the hair switch at $t_0$ ($A_{t0}$) and for the hair at $t_{3h}$ ($A_{t3h}$) and the frizz calculated using the equation given below. Each experiment is repeated with 3 hair switches. The percent Frizz is calculated using below equation:

$$\% \text{ Frizz}=100\times(A_{t3h}\text{-}A_{t0}/A_{t0})$$

$$\% \text{ Frizz reduction}=100\times(\% \text{ Frizz(present invention composition)}-\% \text{ Frizz(control composition)}/\% \text{ Frizz(control composition)}$$

The standard error for Frizz measurement is less than 0.1.
Correlation of % Frizz Reduction Vs % Water Reduction Determined by DVS Methodology Results obtained from DVS measurements and the results from the determination of the frizz reduction methodology of various switches indicate that there is a correlation between the two methods. In other words, hair switches that show low water reduction also show lower frizz as shown in FIG. 1.

FIG. 1 depicting correlation of % water reduction vs % frizz reduction, where hair switches with different dosage are treated and their % water reduction and % frizz reduction is measured using DVS and frizz method respectively.

FIG. 1 is a plot depicting that there is a monotonic correlation between % water reduction and % frizz reduction. As material dosage increases, % water reduction increase resulting in increase in % frizz reduction i.e. more frizz control.

Results

As FIG. 1 demonstrates, there is a monotonic correlation between % water reduction and % frizz reduction. As material dosage increases, more material penetrates into hair, The % water reduction at high humidity increases resulting in an increase in % frizz reduction i.e. more frizz control. This confirms the present invention's technical hypothesis of material penetration, interaction with hair protein and decrease of water uptake inside hair at high humidity resulting in frizz control.

Leave-on Treatment Composition Preparation:

The leave-on treatment compositions are prepared by adding the Moisture Control Materials and perfume, if needed, into a 50:50 ethanol/water carrier and stirred until complete dissolution. The solution pH is adjusted using sodium hydroxide (50% w/w) to a final pH of 4.0-4.2. The Sepigel 305 is then added, if needed, and the solution is mixed using a high-speed-mixer for 2-5 minutes at 1800-2300 rpm until a uniform composition is obtained.

Leave-on Hair Treatment Protocol:

An amount of 0.20 g of each composition of Examples I to IV is spread via a syringe onto separate natural virgin brown hair switches weighing 2.0 g (dosage 0.10 g of solution per g of hair). The hair is allowed to air dry and then analyzed using the DVS method described above. The experiment is repeated for a dosage of 0.50 g of solution per g of hair. The hair in this case is also assessed by expert graders, as described below, in addition to the DVS analysis.

Hair Switch Feel Assessment Method:

The treated hair switches are kept at high humidity (above 85% RH) for 2 hrs and then ten expert graders are asked to rate each of them in terms of tactile feel based on a 5 point scale, 5 being the highest (best feel) and 1 being the lowest rating.

Leave-on Treatment Formulation:

| Raw Material | Leave-on treatment Control (wt./wt.) % | I (wt./wt.) % | II (wt./wt.) % | III (wt./wt.) % | IV (wt./wt.) % | V (wt./wt.) % | VI (wt./wt.) % | VII (wt./wt.) % |
|---|---|---|---|---|---|---|---|---|
| Distilled Water | QS | QS | QS | QS | QS | QS | QS | QS |
| Ethanol | 50.00 | 50.00 | 50.00 | 50.00 | 50.00 | 50.00 | 50.00 | 50.00 |
| Polyacrylamide & C13-14 Isoparaffin & Laureth-7 (Sepigel 305) | 1.85 | 1.85 | 1.85 | 1.85 | 1.85 | 1.85 | 1.85 | 1.85 |
| Perfume | 0.46 | 0.46 | 0.46 | 0.46 | 0.46 | 0.46 | 0.46 | 0.46 |
| Salicylic acid | 0 | 2.0 | 0 | 0 | 2.0 | 2.0 | 0.0 | 0.0 |
| 5-Chlorosalicylic acid | 0 | 0 | 2.0 | 0 | 0 | 0 | 2.0 | 2.0 |
| 2,4-Dihydroxybenzoic acid | 0 | 0 | 0 | 2.0 | 0.15 | 0.15 | 0.15 | 0.15 |
| Oleic acid | 0 | 0 | 0 | 0 | 0 | 0.25 | 0 | 0.25 |
| 2-Hexyl-1-decanol | 0 | 0 | 0 | 0 | 0 | 0.25 | 0 | 0.25 |
| Final pH | 4.2 | 4.2 | 4.2 | 4.2 | 4.2 | 4.2 | 4.2 | 4.2 |
| % Water Reduction versus Leave-on Treatment Control at dose of 0.10 g of composition for 1.0 g of hair | — | — | — | — | 4 | 5 | 5 | 7 |
| % Water Reduction versus Leave-on Treatment Control at dose of 0.50 g of composition for 1.0 g of hair. Control is dosed at 0.50 g of composition for 1.0 g of hair | — | 4 | 5 | 5 | 9 | 8 | 10 | 10 |
| Feel Rating Leave-on Treatment Control at dose of 0.10 g of composition for 1.0 g of hair | 1 | 1 | 2 | 2 | 2 | 3 | 2 | 4 |

| Raw Material | Formula Example | | | | | |
|---|---|---|---|---|---|---|
| | VIII | IX | X | XI | XII | XIII |
| Distilled Water | QS | QS | QS | QS | QS | QS |
| Ethanol | 50.0 | 50.0 | 50.0 | 50.0 | 50.0 | 50.0 |
| 5-Chlorosalicylic acid | 1.0 | | | 1.0 | 1.0 | 1.0 |
| 2-Hexyl-1-decanol | | | 5.0 | 5.0 | | 5.0 |
| Isostearyl Isostearate | | 2.0 | | | 2.0 | 2.0 |
| Final pH | 4 | 4 | 4 | 4 | 4 | 4 |
| % Water Reduction versus Leave-on Treatment Control at dose of 0.10 g of composition for 1.0 g of hair | 1.3 | 0.7 | 1.0 | 2.0 | 1.4 | 3.0 |
| Feel Rating (on 5 scale point with 5 as highest and 1 as lowest) | 1 | 2 | 2 | 3 | 3 | 4 |

Results:

Formula I to XIII showed % water reduction at high humidity. Higher % water reductions are observed in hair treated with higher doses of leave-on Formulas I-XIII The feel assessment results indicate that combinations of
(a) 5-Chlorosalicylic acid and 2-hexyl-1-decanol;
(b) 5-Chlorosalicylic acid and isostearyl isostearate;
(c) 5-Chlorosalicylic acid and 2-hexyl-1-decanol and isostearyl isostearate provide, not only water absorption reduction (resulting in frizz benefit), but also tactile feel benefit. This is shown by the feel comparisons of (a) Example XI versus Examples VIII and IX, (b) Example XII versus Examples VIII and X, and (c) Example XIII versus Examples VIII, IX and X.

Additional Evaluations

Additional leave-on treatment compositions are prepared (Tables 1 and 2) according to the procedure described above, which are used to treat hair switches using the procedure described above (amount of 0.10 g of composition per g of hair). The switch is kept at high humidity (above 85%) for 2 hours. Then, ten experts are asked to rate each hair switch in terms of frizz, clean feel, and greasy feel, based on a 5 point scale, 5 being the highest and 1 being the lowest rating. Acceptable values are:

For frizz, less than 2 (lower number corresponds to less frizz);
For no greasy feel less than 3, (lower number corresponds to less greasy feel), and
For clean feel greater than 3 (higher number corresponds to cleaner feel).

TABLE 1

| | Class I Compounds | | | | | |
|---|---|---|---|---|---|---|
| | Formula Example | | | | | |
| Raw Material | Control | XIV | XV | XVI | XVII | XVIII |
| Distilled Water | 50.0% | 49.5% | 49.5% | 49.5% | 49.5% | 49.5% |
| Ethanol | 50.0% | 49.5% | 49.5% | 49.5% | 49.5% | 49.5% |
| 5-Chlorosalicylic acid | 0% | 1% | 0% | 0% | 0% | 0% |
| Salicylic acid | 0% | 0% | 1% | 0% | 0% | 0% |
| 4-Hydroxybenzenesulphonic acid | 0% | 0% | 0% | 1% | 0% | 0% |
| 2,4-Dihydroxybenzoic acid | 0% | 0% | 0% | 0% | 1% | 0% |
| Terminal Amino Silicone | 0% | 0% | 0% | 0% | 0% | 1% |
| Composition pH adjusted to | 4.2 | 4.2 | 4.2 | 4.2 | 4.2 | 4.2 |
| Greasy Feel | 2 | 1 | 2 | 2 | 2 | 4 |
| Frizz | 4 | 2 | 1 | 2 | 2 | 3 |
| Clean Feel | 4 | 4 | 3 | 4 | 4 | 1 |

Results of Hair Switch Rating from Class I Molecules:

Molecules (5-chlorosalicylic acid, salicylic acid, 4-hydroxybenzenesulphonic acid, 2,4-dihydroxybenzoic acid) from Class I provide hair benefits. More specifically, Table 1 shows that hair treatments with 5-chlorosalicyclic acid, salicylic acid, 4-hydroxybenzenesulfonic acid and 2,4-dihydroxybenzoic acid provide fizz protection with clean feel and without greasy feel negative, as opposed to treatment with terminal aminosilicone, which provide some frizz benefit but with greasy feel negative and significantly less clean feel.

TABLE 2

| | Class II Compounds | | | | | |
|---|---|---|---|---|---|---|
| | Formula Example | | | | | |
| Raw Material | Control | XIX | XX | XXI | XXII | XXIII |
| Distilled Water | 50.0% | 49.5% | 49.5% | 49.5% | 49.5% | 49.5% |
| Ethanol | 50.0% | 49.5% | 49.5% | 49.5% | 49.5% | 49.5% |
| Isostearyl isostearate | 0% | 1% | 0% | 0% | 0% | 0% |
| 2-Hydroxyethyl salicylate | 0% | 0% | 1% | 0% | 0% | 0% |
| Octyl salicylate | 0% | 0% | 0% | 1% | 0% | 0% |
| 2-Hexyl-1-decanol | 0% | 0% | 0% | 0% | 1% | 0% |

TABLE 2-continued

Class II Compounds

| | | | Formula Example | | | |
|---|---|---|---|---|---|---|
| Raw Material | Control | XIX | XX | XXI | XXII | XXIII |
| Terminal Amino Silicone | 0% | 0% | 0% | 0% | 0% | 1% |
| Composition pH adjusted to | 4.2 | 4.2 | 4.2 | 4.2 | 4.2 | 4.2 |
| Greasy Feel | 2 | 2 | 2 | 2 | 3 | 4 |
| Frizz | 4 | 2 | 2 | 1 | 1 | 3 |
| Clean Feel | 4 | 3 | 3 | 3 | 3 | 1 |

Results of Hair Switch Rating from Class II Molecules:

Molecules (Isostearyl isostearate, 2-hydroxylethyl salicylate, octyl salicylate, 2-hexyl-1-decanol) from Class II provide hair benefits. More specifically, Table 2 shows that hair treatment with isostearyl isostearate, 2-hydroxyethyl salicylate, octyl salicylate, and 3-hexyl-1-decanol provide frizz protection with clean feel and without greasy feel negative, as opposed to treatment with terminal aminosilicone, which provide some frizz benefit but with greasy feel negative and significantly less clean feel.

Evaluation of Hair Friction

Leave-on formulation containing Moisture Control Material and Silicone oil shows improvement in dry feel compared to untreated hair. This is concluded by measurement of dry hair friction. For this evaluation, natural virgin brown hair switches (4.0 g) are washed with clarifying shampoo, and then treated with leave-on treatment of composition XXIV according to the protocol described above. Before the evaluation, the switches are air dried overnight in a controlled temperature and humidity room (22° C./50% RH). The friction force (grams) between the hair surface and a urethane pad along the hair is measured, with three measurements per switch using an Instron Tester instrument (Instron 5542, Instron, Inc, Canton, Mass., USA).

TABLE 3

Hair Friction

| | Formula Example | |
|---|---|---|
| Raw Material | XXIV | Control Hair - No Treatment |
| Distilled Water | 49.5% | |
| Ethanol | 49.5% | |
| 2,4 dihydroxybenzoic acid | 1% | |
| Silicone oil | 0% | |
| Composition pH adjusted to | 4.2 | |
| Average Force (g) | 40 | 55 |

As Table 3 indicates, treatment of hair with leave-on composition containing Moisture Control material and silicone oil results in reduced hair friction, which indicates improved dry feel.

It is known that organic hydrophobic molecules that are naturally present inside the hair (e.g. as part of Cell Membrane Complex lipids) contribute to its strength and integrity. It is also known that cosmetic treatments, such as oxidative coloring and permanent shaping result in reduction of the concentration of such hydrophobic material from hair. Thus, penetration of hydrophobic materials (e.g. Class II materials) inside the hair can contribute to lipid replenishment, which, at the same time, reduces water uptake to deliver moisture or frizz control benefit. Combination of different Class II materials e.g. benzyl alcohol, 2-hexyl-1-decanol, isostearyl isostearate, have multi-functionality of penetration, getting embedded into lipid of hair and also increasing the penetration of other hydrophobic materials like oleic resulting in further increase hydrophobicity of the hair interior.

Penetration of Moisture Control Material Inside the Hair

In an embodiment of the present invention, compositions can comprise of glycols, polyglycols, urea, ethers or mixture thereof. These materials increase penetration of moisture control actives such as salicylic acid, 5-chloro salicylic acid, improving their performance. Propylene glycol, butylene glycol and other glycols, increase penetration of 5-chlorosalicylic acid inside hair as it acts as carrier for the actives to penetrate further. As active penetration increases, there is an increase in efficacy of the active, i.e. there is increase in % water reduction as shown below in Table 4. Table 4 shows the amount of 5-chlorosalicylic acid that penetrates inside oxidatively damaged hair after hair treatment with two different compositions. It also shows the % water reduction observed after the treatment versus treatment with control leave-on treatment compositions. These results demonstrate that 5-chlorosalicylic acid penetrates 4 times more in the presence of propylene glycol and there is an increase in % water reduction as measured by DVS of approximate 4 times more than without propylene glycol. Another example of material that enhances the penetration of moisture control material is 2-hydroxyethyl urea. Leave on treatment composition that contain 2% of 2-hydroxyethyl urea increases the penetration of salicylic acid inside hair by 14% compared to the corresponding composition that does not contain 2-hydroxyethyl urea (see example XXVII and XXVIII).

TABLE 4

Enhancing of hair penetration of Moisture Control Material in oxidatively damaged (bleached) Caucasian hair

| | Formula Example | | | | |
|---|---|---|---|---|---|
| Raw Material | Control | XXV | XXVI | XXVII | XXVIII |
| Distilled Water | 50.0% | 48.93% | 43.9% | 48.93% | 48.00% |
| Ethanol | 50.0% | 48.93% | 43.9% | 48.93% | 48.00% |

TABLE 4-continued

Enhancing of hair penetration of Moisture Control Material in oxidatively damaged (bleached) Caucasian hair

| Raw Material | Control | XXV | XXVI | XXVII | XXVIII |
|---|---|---|---|---|---|
| 5-Chlorosalicylic acid | 0.0% | 2.0% | 2.0% | 0.0% | 0.0% |
| 2-hydroxyethyl urea | 0.0% | 0.0% | 0.0% | 0.0% | 2.0% |
| Salicylic acid | 0.0% | 0.0% | 0.0% | 2.0% | 2.0% |
| 2,4-Dihydroxybenzoic acid | 0.0% | 0.15% | 0.15% | 0.0% | 0.0% |
| Propylene glycol | 0.0% | 0% | 10% | 0% | 0.0% |
| Composition pH adjusted to | 4.2 | 4.2 | 4.2 | 4.2 | 4.2 |
| % Water Reduction versus control treatment | — | 0.67% | 3% | — | — |
| Amount of 5-chlorosalicylic acid inside the hair (mg/g of hair) | — | 1 | 3.97 | — | — |
| Amount of Salicylic acid inside hair (mg/g of hair) after 5 cycles | — | — | — | 4.7 | 5.6 |

The penetration amount of 5-chlorosalicylic acid is determined using the following protocol. Each hair tress is extracted 3 times with 0.1% TFA (Trifluoroacetic acid) in methanol and the individual extracts are analyzed separately using HPLC method.

In addition to the increase of the penetration amount of the moisture control material, the presence of glycol in the composition prevents the crystallization of part of the moisture control material in the surface of the hair. Such crystallization causes a non-smooth, negative hair feel, which may be perceived by consumers as hair damage or lack of conditioning.

It has been observed that in an embodiment of the present invention the presence of propylene glycol may provide penetration enhancement for Molecular Class I and Class II materials.

Conditioner Composition

The personal care composition of the present invention comprises a cationic surfactant, high melting point fatty compound, and aqueous carrier. The surfactants, the high melting point fatty compounds, and the aqueous carrier are in the form of emulsion.

Cationic Surfactant System

The composition of the present invention comprises a cationic surfactant system. The cationic surfactant system can be one cationic surfactant or a mixture of two or more cationic surfactants. Preferably, the cationic surfactant system is selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt The cationic surfactant system is included in the composition at a level by weight of from about 0.1% to about 10%, preferably from about 0.5% to about 8%, more preferably from about 0.8% to about 5%, still more preferably from about 1.0% to about 4%.

Mono-Long Alkyl Quaternized Ammonium Salt

The monoalkyl quaternized ammonium salt cationic surfactants useful herein are those having one long alkyl chain which has from 12 to 30 carbon atoms, preferably from 16 to 24 carbon atoms, more preferably C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof. Non-limiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Di-Long Alkyl Quaternized Ammonium Salt

Di-long alkyl quaternized ammonium salt is preferably combined with a mono-long alkyl quaternized ammonium salt or mono-long alkyl amidoamine salt. It is believed that such combination can provide easy-to-rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of preferably from about 10% to about 50%, more preferably from about 30% to about 45%.

The dialkyl quaternized ammonium salt cationic surfactants useful herein are those having two long alkyl chains having 12-30 carbon atoms, preferably 16-24 carbon atoms, more preferably 18-22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

(II)

wherein two of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof. Such dialkyl quaternized ammonium salt cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride. Such dialkyl quaternized ammonium salt cationic surfactants also include, for example, asymmetric dialkyl quaternized ammonium salt cationic surfactants.

High Melting Point Fatty Compound

The high melting point fatty compound useful herein has a melting point of 40° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than 25° C. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992. Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched-chain alcohols. Preferred fatty alcohols include, for example, cetyl alcohol, stearyl alcohol, behenyl alcohol, and mixtures thereof.

High melting point fatty compounds of a single compound of high purity are preferred. Single compounds of pure fatty alcohols selected from the group of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

The high melting point fatty compound is included in the composition at a level of from about 0.1% to about 20%, preferably from about 1% to about 15%, more preferably from about 1.5% to about 8% by weight of the composition, in view of providing improved conditioning benefits such as slippery feel during the application to wet hair, softness and moisturized feel on dry hair.

Aqueous Carrier

The gel matrix of the hair care composition of the present invention includes an aqueous carrier. Accordingly, the formulations of the present invention can be in the form of pourable liquids (under ambient conditions). Such compositions will therefore typically comprise an aqueous carrier, which is present at a level of from about 20 wt. % to about 95 wt. %, or even from about 60 wt. % to about 85 wt. %. The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful in the present invention includes water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

According to embodiments of the present invention, the hair care compositions may have a pH in the range from about 2 to about 10, at 25° C. In one embodiment, the hair care composition has a pH in the range from about 2 to about 6, which may help to solubilize minerals and redox metals already deposited on the hair. Thus, the hair care composition can also be effective toward washing out the existing minerals and redox metals deposits, which can reduce cuticle distortion and thereby reduce cuticle chipping and damage.

Gel Matrix

The composition of the present invention comprises a gel matrix. The gel matrix comprises a cationic surfactant, a high melting point fatty compound, and an aqueous carrier.

The gel matrix is suitable for providing various conditioning benefits such as slippery feel during the application to wet hair and softness and moisturized feel on dry hair. In view of providing the above gel matrix, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:6.

Additional Components

Silicone Conditioning Agent

The compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the polymer can be in an emulsified form with droplet size of about 10 nm to about 30 micrometers Other solid or semi-solid conditioning agents may be present in the composition including high melting temperature fatty alcohols, acids, esters, amides or oligomers from unsaturated esters, alcohols, amides. The oligomeric esters may be the result of oligomerization of naturally-occuring unsaturated glyceride esters. Such solid or semi-solid conditioning agents may be added or present as mixtures with organic oils.

Nonionic Polymers

The hair care composition of the present invention may also further comprise a nonionic polymer. According to an embodiment, the conditioning agent for use in the hair care composition of the present invention may include a polyalkylene glycol polymer. For example, polyalkylene glycols having a molecular weight of more than about 1000 are useful herein. Useful are those having the following general formula (VIII):

wherein $R^{11}$ is selected from the group consisting of H, methyl, and mixtures thereof; and v is the number of ethoxy units. The polyalkylene glycols, such as polyethylene glycols, can be included in the hair care compositions of the present invention at a level of from about 0.001 wt. % to about 10 wt. %. In an embodiment, the polyethylene glycol is present in an amount up to about 5 wt. % based on the weight of the composition. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000, and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

Organic Conditioning Materials

The conditioning agent of the compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Deposition Aids

The hair care compositions of the present invention may further comprise a deposition aid, such as a cationic polymer. Cationic polymers useful herein are those having an average molecular weight of at least about 5,000, alternatively from about 10,000 to about 10 million, and alternatively from about 100,000 to about 2 million.

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. Other suitable spacer monomers include vinyl esters, vinyl alcohol (made by hydrolysis of polyvinyl acetate), maleic anhydride, propylene glycol, and ethylene glycol. Other suitable cationic polymers useful herein include, for example, cationic celluloses, cationic starches, and cationic guar gums.

The cationic polymer can be included in the hair care compositions of the present invention at a level of from about 0.001 wt. % to about 10 wt. %. In one embodiment, the cationic polymer is present in an amount up to about 5 wt % based on the weight of the composition.

Benefit Agents

In an embodiment, the hair care composition further comprises one or more additional benefit agents. The benefit agents comprise a material selected from the group consisting of anti-dandruff agents, anti-fungal agents, anti-itch agents, anti-bacterial agents, anti-microbial agents, moisturization agents, anti-oxidants, vitamins, lipid soluble vitamins, chelants, perfumes, brighteners, enzymes, sensates, attractants, dyes, pigments, bleaches, and mixtures thereof. In one aspect said benefit agent may comprise an anti-dandruff agent. Such anti-dandruff particulate should be physically and chemically compatible with the components of the composition, and should not otherwise unduly impair product stability, aesthetics or performance.

According to an embodiment, the hair care composition comprises an anti-dandruff active, which may be an anti-dandruff active particulate. In an embodiment, the anti-dandruff active is selected from the group consisting of: pyridinethione salts; azoles, such as ketoconazole, econazole, and elubiol; selenium sulphide; particulate sulfur; keratolytic agents such as salicylic acid; and mixtures thereof. In an embodiment, the anti-dandruff particulate is a pyridinethione salt. Pyridinethione particulates are suitable particulate anti-dandruff actives. In an embodiment, the anti-dandruff active is a 1-hydroxy-2-pyridinethione salt and is in particulate form. In an embodiment, the concentration of pyridinethione anti-dandruff particulate ranges from about 0.01 wt. % to about 5 wt. %, or from about 0.1 wt. % to about 3 wt. %, or from about 0.1 wt. % to about 2 wt. %. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, fcharcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof. In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the hair care composition, the azole anti-microbial active is included in an amount of from about 0.01 wt. % to about 5 wt. %, or from about 0.1 wt. % to about 3 wt. %, or from about 0.3 wt. % to about 2 wt. %. In an embodiment, the azole anti-microbial active is ketoconazole. In an embodiment, the sole anti-microbial active is ketoconazole.

Embodiments of the hair care composition may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the composition comprises an effective amount of a zinc-containing layered material. In an embodiment, the composition comprises from about 0.001 wt. % to about 10 wt. %, or from about 0.01 wt. % to about 7 wt. %, or from about 0.1 wt. % to about 5 wt. % of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_{1-x}(OH)_2]^{x+}A^{m-}_{x/m}.nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42). Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1-x}M^{3+}_{1-x}(OH)_{3(1-y)}]^+A^{n-}_{(1=3y)/n}\cdot nH_2O$ where the two metal ions ($M^{2\pm}$) may be the same or different. If they are the same and represented by zinc, the formula simplifies to $[Zn_{1+x}(OH)_2]^{2x+}2\times A^-\cdot nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

The on-scalp deposition of the anti-dandruff active is at least about 1 microgram/cm². The on-scalp deposition of the anti-dandruff active is important in view of ensuring that the anti-dandruff active reaches the scalp where it is able to perform its function. In an embodiment, the deposition of the anti-dandruff active on the scalp is at least about 1.5 microgram/cm², or at least about 2.5 microgram/cm², or at least about 3 microgram/cm², or at least about 4 microgram/cm², or at least about 6 microgram/cm², or at least about 7 microgram/cm², or at least about 8 microgram/cm², or at least about 8 microgram/cm², or at least about 10 microgram/cm². The on-scalp deposition of the anti-dandruff active is measured by having the hair of individuals washed with a composition comprising an anti-dandruff active, for example a composition pursuant to the present invention, by trained a cosmetician according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

Carrier

The composition of the present invention may comprise an aqueous carrier. The level and species of the carrier are selected according to the compatibility with other components, and other desired characteristic of the product.

The carrier useful in the present invention includes water and water solutions of lower alkyl alcohols. The lower alkyl alcohols useful herein are monohydric alcohols having 1 to 6 carbons, and in a further embodiment, ethanol and isopropanol.

In an embodiment of the present invention, the aqueous carrier is substantially water. In a further embodiment, deionized water may be used. Water from natural sources including mineral cations can also be used, depending on the desired characteristic of the product. Generally, the compositions of the present invention comprise from about 0% to about 99%, in an embodiment from about 50% to about 95%, in a further embodiment from about 70% to about 90%, and in a further embodiment from about 80% to about 90% water.

Rheology Modifier/Suspending Agents

In one embodiment, the rinse-off conditioner composition comprises a rheology modifier. The rheology modifier increases the substantivity and stability of the composition, improve feel and consumer's use experience (e.g. non-dripping, spreadability, etc). Any suitable rheology modifier can be used. In an embodiment, the hair care composition may comprise from about 0.05% to about 10% of a rheology modifier, in a further embodiment, from about 0.1% to about 10% of a rheology modifier, in yet a further embodiment, from about 0.5% to about 2% of a rheology modifier, in a further embodiment, from about 0.7% to about 2% of a rheology modifier, and in a further embodiment from about 1% to about 1.5% of a rheology modifier. In an embodiment, the rheology modifier may be a polyacrylamide thickener. In an embodiment, the rheology modifier may be a polymeric rheology modifier.

In one embodiment, the rinse-off conditioner composition may comprise rheology modifiers that are homopolymers based on acrylic acid, methacrylic acid or other related derivatives, non-limiting examples include polyacrylate, polymethacrylate, polyethylacrylate, and polyacrylamide.

In another embodiment, the rheology modifiers may be alkali swellable and hydrophobically-modified alkali swellable acrylic copolymers or methacrylate copolymers non-limiting examples include acrylic acid/acrylonitrogen copolymer, acrylates/steareth-20 itaconate copolymer, acrylates/ceteth-20 itaconate copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/vinylneodecanoate crosspolymer, and acrylates/C10-C30 alkyl acrylate crosspolymer.

In a further embodiment, the rheology modifiers may be crosslinked acrylic polymers, a non-limiting example includes carbomers.

In a father embodiment, the rheology modifiers may be alginic acid-based materials; non-limiting examples include sodium alginate, and alginic acid propylene glycol esters.

In a further embodiment, the rheology modifier may be an associative polymeric thickeners, non-limiting examples include: Hydrophobically modified cellulose derivatives; Hydrophobically modified alkoxylated urethane polymers, nonlimiting example include PEG-150/decyl alcohol/SMDI copolymer, PEG-150/stearyl alcohol/SMDI copolymer, polyurethane-39; Hydrophobically modified, alkali swellable emulsions, non-limiting examples include hydrophobically modified polyacrylates, hydrophobically modified polyacrylic acids, and hydrophobically modified polyacrylamides; hydrophobically modified polyethers wherein these materials may have a hydrophobe that can be selected from cetyl, stearyl, oleayl, and combinations thereof, and a hydrophilic portion of repeating ethylene oxide groups with repeat units from 10-300, in another embodiment from 30-200, in a further embodiment from 40-150. Non-limiting examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

In a further embodiment, the rheology modifier may be cellulose and derivatives; nonlimiting examples include microcrystalline cellulose, carboxymethylcelluloses, hydroxyethylcellulose, hydroxypropylcellulose, hydroxypropylmethylcellulose, methylcellulose, ethylcellulose, nitro cellulose, cellulose sulfate, cellulose powder, and hydrophobically modified celluloses In an embodiment, the rheology modifier may be a guar and guar derivatives; nonlimiting examples include hydroxypropyl guar, and hydroxypropyl guar hydroxypropyl trimonium chloride. In an embodiment, the rheology modifier may be polyethylene oxide, polypropylene oxide, and POE-PPO copolymers.

In an embodiment, the rheology modifier may be polyvinylpyrrolidone, crosslinked polyvinylpyrrolidone and derivatives. In a further embodiment, the rheology modifier may be polyvinyalcohol and derivatives.

In a further embodiment, the rheology modifier may be polyethyleneimine and derivatives.

In another embodiment, the rheology modifier may be silicas; nonlimiting examples include fumed silica, precipitated silica, and silicone-surface treated silica.

In an embodiment, the rheology modifier may be water-swellable clays non-limiting examples include laponite, bentolite, montmorilonite, smectite, and hectonite.

In an embodiment, the rheology modifier may be gums nonlimiting examples include xanthan gum, guar gum, hydroxypropyl guar gum, Arabia gum, tragacanth, galactan, carob gum, karaya gum, and locust bean gum.

In a further embodiment, the rheology modifier may be, dibenzylidene sorbitol, karaggenan, pectin, agar, quince seed (*Cydonia oblonga* Mill), starch (from rice, corn, potato, wheat, etc), starch-derivatives (e.g. carboxymethyl starch, methylhydroxypropyl starch), algae extracts, dextran, succinoglucan, and pulleran.

In an embodiment, the composition of the present invention may comprise suspending agents including crystalline suspending agents which can be categorized as acyl derivatives, long chain amine oxides, and mixtures thereof. These suspending agents are described in U.S. Pat. No. 4,741,855. These suspending agents include ethylene glycol esters of fatty acids in one aspect having from about 16 to about 22 carbon atoms. In one aspect, useful suspending agents include ethylene glycol stearates, both mono and distearate, but in one aspect, the distearate containing less than about 7% of the mono stearate. Other suitable suspending agents include alkanol amides of fatty acids, having from about 16 to about 22 carbon atoms, or even about 16 to 18 carbon atoms, examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin® R available from Rheox, Inc. Long chain acyl derivatives, ethylene glycol esters of long chain carboxylic acids, long chain amine oxides, and alkanol amides of long chain carboxylic acids in addition to the materials listed above may be used as suspending agents. Other long chain acyl derivatives suitable for use as suspending agents include N,N-dihydrocarbyl amido benzoic acid and soluble salts thereof (e.g., Na, K), particularly N,N-di(hydrogenated) C16, C18 and tallow amido benzoic acid species of this family, which are commercially available from Stepan Company (Northfield, Ill., USA). Examples of suitable long chain amine oxides for use as suspending agents include alkyl dimethyl amine oxides, e.g., stearyl dimethyl amine oxide. Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Non-limiting examples of rheology modifiers include acrylamide/ammonium acrylate copolymer (and)polyisobutene (and) polysorbate 20, acrylamide/sodium acryloyldimethyl taurate copolymer/isohexadecane/polysorbate 80, acrylates copolymer; acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil, C12-16 alkyl PEG-2 hydroxypropylhydroxyethyl ethylcellulose (HM-EHEC), carbomer, cros slinked polyvinylpyrrolidone (PVP), dibenzylidene sorbitol, hydroxyethyl ethylcellulose (EHEC), hydroxypropyl methylcellulose (HPMC), hydroxypropyl methylcellulose (HPMC), hydroxypropylcellulose (HPC), methylcellulose (MC), methylhydroxyethyl cellulose (MEHEC), PEG-150/decyl alcohol/SMDI copolymer, PEG-150/stearyl alcohol/SMDI copolymer, polyacrylamide/C13-14 isoparaffin/laureth-7; polyacrylate 13/polyisobutene/polysorbate 20; polyacrylate crosspolymer-6, polyamide-3; polyquaternium-37 (and) hydrogenated polydecene (and) trideceth-6, polyurethane-39, sodium acrylate/acryloyldimethyltaurate/dimethylacrylamide, crosspolymer (and) isohexadecane (and) polysorbate 60; sodium polyacrylate. Exemplary commercially-available rheology modifiers include ACULYN™ 28, Klucel™ M CS, Klucel™ H CS, Klucel™ G CS, SYLVACLEAR™ AF1900V, SYLVACLEAR™ PA1200V, Benecel™ E10M, Benecel™ K35M, Optasense™ RMC70, ACULYN™33, ACULYN™46, ACULYN™22, ACULYN™44, Carbopol Ultrez™ 20, Carbopol Ultrez™ 21, Carbopol Ultrez™ 10, Carbopol Ulterez™ 30, Carbopol™ 1342, Carbopol™ 934, Carbopol™ 940, Carbopol™ 950, Carbopol™ 980, and Carbopol™ 981, Acrysol™ 22, Sepigel™ 305, Simulgel™600, Sepimax Zen, and combinations thereof.

It is further noted that terms like "alternatively," "usually", "generally," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

What is claimed is:

1. A rinse-off conditioner composition for hair frizz reduction comprising: from about 0.2% to about 20% of a moisture control material or mixture of moisture control materials, wherein the moisture control material comprises salicylic acid in combination 2,4-dihydroxybenzoic acid, and wherein the rinse-off conditioner composition further comprises a material selected from the group consisting of glycols, polyglycols, 2-hydroxyethyl urea and mixture thereof.

2. A rinse-off conditioner composition according to claim 1 wherein the concentration of the Moisture Control Material or the concentration of the mixture of Moisture Control Material is from about 0.5% to about 8%.

3. A rinse-off conditioner composition according to claim 1 wherein the concentration of the Moisture Control Material or the concentration of the mixture of Moisture Control Material is from about 0.5% to about 5%.

4. A rinse-off conditioner composition according to claim 1 wherein there is a 15% frizz reduction vs. control composition without the moisture control material.

5. A rinse-off conditioner composition according to claim 1 wherein there is a 20% frizz reduction vs. control composition without the moisture control material.

6. A rinse-off conditioner composition according to claim 1 wherein the moisture control material further comprises 5-chlorosalicylic acid.

7. A rinse-off conditioner composition according to claim 1 further comprising 5-chlorosalicylic acid and propylene glycol.

8. A rinse-off conditioner composition according to claim 1 further comprising 5-chlorosalicylic acid in combination with and silicone.

9. A composition according to claim 1 comprising salicylic acid from about 0.5% to about 2% in combination with 2-hydroxyethyl urea from about 0.2% to about 10%.

10. A rinse-off conditioner composition according to claim 1 wherein the pH is in the range of about 2 to about 7.

11. A rinse-off conditioner composition according to claim 1 wherein the pH is in the range of about 2 to about 5.

12. A rinse-off conditioner composition according to claim 1 wherein the composition further comprises a silicone.

13. A rinse-off conditioner composition according to claim 1 wherein the composition further comprises materials selected from the group consisting of conditioning materials, organic conditioning materials, solvents, rheology modifier, suspending agent, thickeners, hair health actives, anti-dandruff actives, anti-oxidants, pigments, abrasives, absorbents, biological actives, buffering agents, chelating agents, opacifying agents, pH adjusters, vitamins, chelants, perfumes, brighteners, enzymes, sensates, attractants, anti-bacterial agents, dyes, bleaches and mixtures thereof.

14. A rinse-off conditioner composition according to claim 1 wherein the composition further comprises a cationic surfactant system.

15. A rinse-off conditioner composition according to claim 1 wherein the conditioner composition further comprises:
   i. from about 0.1% to about 20% of one or more high melting point fatty compounds, by weight of said hair care composition;
   ii. from about 0.1% to about 10% a cationic surfactant system of, by weight of said hair care composition; and
   at least about 20% of an aqueous carrier, by weight of said hair care composition.

16. A rinse-off conditioner composition for hair frizz reduction comprising from about 0.2% to about 20% of a moisture control material or mixture of moisture control materials wherein the moisture control material is a combination of salicylic acid and 2,4-dihydroxybenzoic acid and further wherein there is at least about a 4% frizz reduction vs. a control composition without the moisture control material.

* * * * *